United States Patent [19]

Georgusis

[11] Patent Number: Plant 6,212

[45] Date of Patent: Jun. 28, 1988

[54] EUPHORBIA 'GEORGUSIS NO. 1.'

[76] Inventor: James J. Georgusis, 3714 SW. 52nd Ave., Hollywood, Fla. 33023

[21] Appl. No.: 874,338

[22] Filed: Jun. 13, 1986

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Roger L. Martin

[57] ABSTRACT

A new and distinct variety of Euyphorbia plant of the *milii* group has a very compacy habit with short internodes and very frequent branching that is productive of clavate branches which at the nodes bear persistent long acicular stipular spines. The leaves are oblanceolate to obovate and the plant develops pseudobracts as opposite to subopposite pairs on leafy stems and branches and which subtend a developing leafy branch and/or cyathial branch. The blades of the pseudobracts are usually variegated and have a basic field which in color is usually dominated by a red, purplish red and/or purplish pink hue. The basic field usually has streaks and/or blotches which vary in pattern and size and which in color are usually dominated by a yellow green hue. The inflorescence rarely exceeds three tiers of cyathia and the bract blades of the cyathia are in color dominated by a red and/or purplish red hue. The plant has a growth habit of producing a dense interlocked network of branches that provide a compact domed vegetative crown without the need for pruning from the propagation of but one stem cutting.

8 Drawing Sheets

The invention relates to a new and distinct plant variety of the Euphorbiaceae family and which has been named Euphorbia 'Georgusis No. 1.' by the inventor.

The new variety was found growing as a seedling among others being grown for purposes of investigation and evaluation by the inventor from seeds taken from a specimen of *Euphorbia milii* 'Tricolor'. Since its discovery the new plant variety has been reproduced by the propagation of stem cuttings taken from the original plant. Among other differences, specimens of the 'Tricolor' variety have bract blades of the Cyathium which are wider than those of the new variety and which are usually pale yellow and marbeled with pale crimson in contrast to the vivid red and vivid purplish red colors commonly found in the mature bract blades of the new variety.

The *milii* group of euphorbias is said to be native to Madagascar and "a very complex family of shrub-like plants which are often only distinguished from each other by minor floral characteristics". The *E. milii breoni* is said to have "leaves 10–15 cm long, and 2–3 cm across". By contrast leaves of the new variety are of the order of 2.5–4.5 cm in length and 1.2–1.8 cm in width.

The *E. milii bosseri* is said to have branches "which spread horizontally, are 3–10 mm thick and are green in new growth but become silvery green with age". These branches are said to "bear deciduous lanceolate to linguiform mucronate leaves 3–5 cm in length and 3–5 mm. in width". It is said the inflorescence "consists of 2–4 cymes with each "flower" bearing 2 triangular 3×3 mm light green cyathophylls". By contrast, the branches of the new variety have an upright growth habit and the leaves are oblanceolate to obovate with some evidence of spathulate and elliptic tendencies. The leaves are also somewhat shorter in length and narrower in width, being generally 2.5–4.5 cm long and about 1.2–1.8 cm in maximum width. In addition, the bracts of the cyathium of the new variety are reniform in shape, are usually 3.5–6.5 mm in length and 5–8 mm. in maximum width, and are usually in color dominated by a red and/or purplish red hue when mature and fully expanded.

Specimens of *Euphorbia milii longifolia Rauh* are said to form "a basally branching shrub 80–100 cm tall, with the upright branches being uniformly 1.5–2 cm thich from top to bottom". The branches of this variety are said to send out numerous short shoots which can reach 3 cm in length". Leaves on the longer stems are said to be "1–2 cm long, 8–10 mm wide, mucronate, more or less folded inwardly, and narrow-lanceolate in shape; the leaves on the short shoots" being "rosulate, 3–4 cm long and 5 mm across". As for the inflorescence, it is said to consist "of 1 or several viscous pedicels which bear 4–30 cymes" while the "broadly oval 5 mm long cyathophylls are a pale suphur-yellow in coloration. By way of contrast, the new variety has a zonocaulous branching habit, is productive of clavate branches, and has leaves that are usuially about 2.5–4.5 cm in length and about 1.2–1.8 cm in maximum width. In addition the inflorexcences of the new variety have bracts which in size are seemingly larger, being of the order of magnitude of 5–8 mm in maximum width and 3.5–6.5 mm. in length and, as will be seen, are in color dominated by a red and/or purplish red hue when mature and fully expanded.

The *Euphorbia splendens* (*milii*) "Crown of thorns" is a spiny shrub that has a climbing woody stem that grows "to 2 m long" with "the spreading branches about 1 cm dia., grooved and armed with spines" which are said by some sources to be about "an inch long". Specimens of the variety are said to have "obovate 4 cm leaves" and flower bracts that are "soft salmon-red with pale center". Specimens of the new variety are distinguishable from the "Crown of thorns" in various respects. For one, specimens of the new variety are productive of shorter stems and the spines of the new variety are shorter than those of the "Crown of thorns". Among other things, the new variety may be contrasted with the "Crown of thorns" by a growth habit which from the propogation of a single cutting is productive of a specimen with a dense interlocked network of branches that provide a compact domed vegetative crown without the need for pruning.

The *Euphorbia splendens bojeri* "Dwarf crown-of-thorns" in the literature is said to be a "bushy gray-spined plant of compact habit with upright gray main stem, freely branching, the stubby branches with slender thorns and small persistent dark green leaves about 3 cm long, pale gray-green beneath, and with terminal clusters of flowers with pretty, rounded cardinal red bracts". Insofar as the inventor is aware, this variety, like all the aforementioned *Euphorbia milii* hybrids and varieties lacks the pseudobracts which characterize specimens of the new plant variety and furthermore lacks the growth habit of the new variety and which from a single propagated cutting produces a specimen with a dense interlocked network of branches that provide a compact domed vegetative crown without the need for pruning.

Two patented varieties of the Euphorbia genus are known to the inventor. The subject matter of U.S. Plant Pat. No. 4,761 indicates with respect to the leaves that "they are of varying length and width up to about 15 cm in length and up to about 5 cm in width and usually about 3–4 cm in width". The leaves are said to be "spatulate, with tips varying from very slightly emarginate to very slightly mucronate and an acuminate base". Specimens of the new variety have a leaf size that also varies but which in length is roughly about ¼ that reportred by the patentee and in width is about ½ that reported by the patentee. In addition, the new variety has a general leaf shape that ranges from oblanceolate to obovate with only occasional evidence of spathulate tendencies. Apart from this the pseudobract and compact domed vegetative crown characterists obtainable without pruning would appear to be absent in the patented variety.

The subject matter of U.S. Plant Pat. No. 4,931 describes the leaves of the patented variety as growing "up to about 6–8 cm in length . . . and about 3 cm in width". The pedicels (peduncles) are described as "usually about 4–9 cm in length up to the first ramification and 3–4 mm in thickness". As for the cyathia, the patentee indicates, the "bracts are veined, round, slightly superposed and of a diameter of about 1.5 to 3 cm". By way of contrast specimens of the new plant variety have leaves that are usually in the 2.5–4.5 cm length range and in the 1.2–1.8 cm maximum width range. The primary axes of the peducncles are usually 2.2–4.0 cm and the branches are usually 0.5–2.0 cm. The bracts of the cyathia are, furthermore, smaller than those of the patented variety.

A general object of the invention has been to develop a compact variety of the *Euphorbia milii* group which would be distinguishable from others in the group and through propogation be productive of specimens with a dense interlocked network of branches that provide a compact vegetative crown without the need for pruning.

The object of the invention has been fully realized by the development of the new plant variety described hereafter in detail. Thus, through successive propagations, it has be ascertained that specimens of the new plant variety are distinguishable from those of its antecedents and related varieties known to the inventor by a growth habit which is evident in specimens propagated and grown at Hollywood, Fla. as combining the following principal characteristics:

1. a very compact habit with short internodes and very frequent branching;

2. branches which are clavate and at the nodes bear persistent long acicular stipular spines that are usually 8–12 mm in length;

3. leaves which in shape generally range from oblanceolate to obovate, have relatively short petioles, and have blades that in length are usually 25–45 mm and in maximum width are usually 12–18 mm;

4. pseudobracts which usually develop as opposite to subopposite pairs on a leafy stem or branch and subtend a developing leafy branch and/or cyathial branch and which have blades that are usually variegated and provided with a basic field which in color is usually dominated by a red, purplish red and/or purplish pink hue and has streaks and/or blotches that vary in pattern and size within a pseudobract and from one pseudobract to the next and, in color, are usually dominated by a yellow green hue;

5. an inflorescence which usually has not more than three tiers of cyathia and wherein the blades of the cyathial bracts are in color dominated by a red and/or purplish red hue when mature and fully expandes; and 6. a growth habit which from the propagation of a single stem cutting is productive of a specimen with a dense interlocked network of branches that provide a compact domed vegetative crown without the need for pruning.

The accompanying drawings serve by color photographic means to illustrate the new plant variety and wherein: A first sheet shows a generally side view of a 14 month old potted specimen of the new variety; a second sheet is a close-up view of a portion of the vegetative crown of the specimen seen in the first sheet and illustrates the dense nature of the growth; a third sheet illustrates the pseudobracts and the variant nature of the variegations; a fourth sheet show a primary branch that has been removed from the specimen shown in the first sheet and is presented to illustrate the clavate nature of the branches; a fifth sheet shows a close-up of some foliage seen on the potted specimen show in the first sheet and is presented to show several cyathia in various stages of development including some in the upper right hand corner of the photograph where the bracts are immature and in the process of expanding; and sixth, seventh and eight sheets which are enlargements showing several cyathia in various stages of maturity.

The following is a detailed description of the new plant variety with colors named in caccord with the ISCC-NBS method of designating colors (U.S. Department of Commerce, National Bureau of Standards, Circular 553, issued Nov. 1, 1955) and as interpreted from color notations derived by comparison with color specimens either found in the current edition of the Munsell Book of Color, or in the Munsell Limit Color Cascade, both published by Munsell Color Macbeth, a division of Kollmorgen Corporation, 1441 N. Calvert St., Baltimore, Md. 21218.

In the text herein, the designated ISCC-NBC color name is first set forth and then followed in brackets [ ] with the serial number of the ISCC-NBC color name block therefor. This serial number is, in turn, followed in parentheses ( ) with the Munsell color notation(s) e.g. hue/value/chroma. The Munsell Color notation(s) presented are either those directly read when comparisons were made with the Munsell Book of Color, or as derived by conversion from the two-part number assigned to each color found in the Munsell Limit Color Cascade.

The description is based on observations of well fertilized plants grown under nonshaded conditions in the Hollywood, Fla. area. The plants observed for purposes of the description were approximately six (6) months old at the time of observation and had been propagated from tip stem cuttings that were about 7-12 cm. long at the time of propagation. The observations including the color comparisons were taken during the month of June.

DETAILED PLANT DESCRIPTION

I. Name: Euphorbia 'Georgusis No. 1.'

II. Origin: Hybrid plant arising from an unknown paternal source but found among a group of seedlings derived from a specimen of an *Euphorbia milii* 'Tricolor' and being grown among the inventor's nursery collection for purposes of investigation.

III. Classification:

A. *Botanic.*—Euphorbia Section Euphorbia, Subsection Diacantahium, *hybrida incertae sedis,* Spurge family (Euphorbisceae).

B. *Commercial.*—Flowering pot and ornamental plant.

IV. Plant form: Woody, succulent, tropical, perennial evergreen that has an upright ramose spiny stem with zonocaulous branching which provides primary, secondary, etc. spiny branches with acroramous leaves that form a compact domed vegetative crown, pseudobracts that are frequently variegated and develop as opposite to subopposite developing pairs on a leafy stem and subtending a branch and/or cyathial branch, and cyathium inflorescences that are carried beyond the crown on a usually dichotomously branched peduncle.

V. Plant size (6 months old):

A. *Plant height (above soil level).*—Usually 15-20 cm.

B. *Crown diameter (horizontal).*—Usually 15-25 cm.

C. *Inflorescence length (from axil of subtending leaf).*—Usually 2.5-6.0 cm.

VI. Stems and branches:

A. *General.*—Woody and erect primary stems with many primary ascending lateral branches that have secondary and frequently tertiary ascending lateral branches after a 4-6 month growth period from propagation of the primary stem forming plant part, the stems and branches all bearing persistent spines at each node.

Branches usually originate from an axillary bud which elongates to produce a normal branch, or occasionally by continuation of the terminal bud between a pair of normal inflorescence bracts whose axillary bract buds each of which elongates to produce a pedunculate floriferous cyathium, or, more rarely, by the development of a pair of opposite to subopposite pseudobracts with axillary buds, usually one of the pair producing a vegetative branch while the other develops into a pedunculate floriferous cyathium.

B. *Nodes.*—Short internodal distances, usually less than 3 mm and, in the absence of a leaf insertion, provided with a single broadly obovate leaf scar that subtends a single bud, or an inflorescence or branch insertion or scar, each leaf scar and insertion usually having a pair of long persistent acicular stipular spines located at the opposite sides of the leaf scar or insertion and each long spine usually having 1-3 short spines associated therewith, the short spines associated with the long spines on the branches generally being longer and more numerous the more distal the node location on the branch.

C. *Shape.*—1. Stems: Elongate and terete to widely elliptic in cross section. 2. Branches: Elongate and terete to widely elliptic in cross section, and with the diameter gradually increasing distally of the insertion in the basal structure of most branches, thus being clavate.

D. *Texture (at maturity).*—1. Stems: Glabrous with evident glaucous tendencies and being glaucous and rugulose under magnification (10×). 2. Branches: Glabrous with evident glaucous tendencies and being glaucous and rugulose under magnification (10×).

E. *Size (on 6 month old plant specimens).*—1. Primary axis: (a) Diameter (1-3 cm above soil line). Usually 9-12 mm. (b) Height (above soil line). Usually 10-15 cm. 2. Primary branches: (a) Diameter. Usually 3.5-6 mm near insertion and increasing distally to a maximum of usually 8-10 mm. (b) Length. Usually 6-12.5 cm. 3. Secondary branches: (a) Diameter. Usually 2-3.5 mm near insertion and increasing distally to a maximum of usually 5-8 mm. (b) Length. Usually 3-9 cm. 4. Long spines: Usually 8-12 mm long. 5. Short spines: Usually 1-6 mm long.

F. *Color.*—1. Stems and branches: (a) General. Usually uniform coloration in the leafless and glaucous basal areas and usually dominated by olive, greenish yellow and/or yellow green hues in the leaf bearing apical areas. (b) Basal areas. Commonly yellowish gray [93] (near 2.5 Y 7/2; 5Y 7/1), grayish yellow [90] (near 2.5 Y 7/2). (c) Apical areas. Commonly light olive [106] (10 Y 6/4; 7.5 Y 5/4), dark greenish yellow [103] (10 Y 6/6), moderate greenish yellow [102] (10 Y 7/6) and/or moderate yellow green [120] (2.5 GY 7/6).

VII. Leaves:

A. *General.*—Simple, petiolate and subtended by persistent stipular spines (See: Stem Nodes.) and expanded blades.

B. *Leaf shape.*—1. General: Usually ranging from oblanceolate to obovate but occasionally evidencing spathulate or elliptic tendencies. 2. Leaf apices: Usually cuspidate with uncinate tendencies. 3. Leaf bases: Usually symmetric and attenuate but with an occasional showing of decurrent tendencies. 4. Leaf margins: Entire with revoilute tendencies.

C. *Leaf arrangement.*—Alternate and commonly showing 8/13 phyllotaxy.

D. *Venation.*—1. General. Pinnately netted and brochidodromous with a prominent midrib, secondary viens that are inconspicuous on the adaxial side and barely evident on the abaxial side, the lesser veins being usually visible only by the transmission of light through the specimen. 2. Shape and arrangement (at leaf maturity). (a) Midrib: Tapering distally and being weakly canaliculate in the proximal area of the adaxial side and keeled throughout most of its length on the abaxial side, the abaxial arch being generally semi-elliptic to semi-circular in the proximal area of the midrib and diminishing in both width and height distally thereof while the adaxial groove is a shallow rounded depression in the proximal area of the midrib that distally thereof diminishes in both width and depth and usually becomes obscured by the blade insertions in the distal half of the leaf. (b) Lateral veins: Usually 8–15 secondary veins from each side of the midrib and at spaced intervals which are usually 1.5–3.5 mm apart along the midrib, the tertiary veins forming an obscure net and being spaced apart along the secondary veins at intervals which are usually 0.5–1.5 mm. 3. Midrib color (at leaf maturity): (a) General. Usually concolorous or nearly so with the leaf blades on the adaxial side and usually darker than the abaxial blade surface color. (b) Adaxial side. Commonly strong yellow green [117] (5 GY 5/8), deep yellow green [118] (6.5 GY 3.8/7.1), moderate yellow green [120] (7.5 GY 5/6), moderate olive green [125] (5 GY 4.4; 6.1 GY 3.2/5.8; 7.5 GY 4/4) and/or dark yellowish green [137] (8.2 GY 3.2/6.1). (c) Abaxial side. Commonly moderate yellow green [120] (2.5 GY 5/6; 5 GY 5/6).

E. *Petioles.*—1. General: Short with little differentiation from the base of the midrib. 2. Shape: Terete with tendency to be flattened on the adaxial side. 3. Texture: Glabrous and smooth. 4. Size (at leaf maturity): (a) Diameter. Usually 0.8–1.5 mm. (b) Length. Usually 0.3–1.5 mm to blade insertions. 5. Color (at leaf maturity): (a) General. Usually concolorous with the basal portions of the blade and midrib in the area proximate thereto. (b) Adaxial side. Commonly brilliant yellow green [116] (5 GY 8/8; 5 GY 8/10), light yellow green [119] (5 GY 9/4), moderate yellow green [120] (2.5 GY 7/6; 5 GY 7/6), and/or strong yellow green [117] (2.5 GY 6/8). (c) Abaxial side. Commonly deep greenish yellow [100] (near 10 Y 6/8), dark greenish yellow [103] (near 10 Y 6/8), light yellow green [119] (2.5 GY 8/6), moderate yellow green [120] (5 GY 5/6; 2.5 GY 6/6), and/or strong yellow green [117] (5 GY 5/8).

F. *Leaf blades.*—1. General: Chartaceous with inconspicuous secondary and tertiary veins and some tendencies toward roseous pigmentation at the base and on the revolute portions of the margins. 2. Blade texture: (a) Upper epidermal side. Glabrous with a few scattered flexuose hairs and mildly sulcate along the midrib. (b) Lower epidermal side. Glabrous and weakly glaucous with a few scattered flexuose hairs along the midrib ridge. 3. Blade size (at maturity): (a) Length. Usually 25–45 mm. (b) Width (maximum). Usually 12–18 mm. 4. Blade color (at maturity): (a) General. Basic chlorophyllous field with the adaxial surface being darker than the abaxial surface, and with occasional red pigmentation being evident on revolute marginal portions. (b) Adaxial surface. Commonly deep yellow green [118] (6.5 GY 3.8/7.1), moderate olive green [125] (4.5 GY 3.9/6.9; 5 GY 4/4; 6.1 GY 3.2/5.8; 7.5 GY 4/4; 5 GY 4/4) in the basic field and dark purplish red [259] (10 RP 3/6), grayish red [19] (2.5 R 4/6) and/or moderate red [15] (2.5 R 4/8) in revolute marginal portions when pigmentation becomes evident. (c) Abaxial surface. Commonly strong yellow green [117] (2.5 GY 4.6/7.7; 3.3 GY 5.0/8.8; 5.3 GY 5.2/9.7), moderate yellow green [120] (5 GY 6/6; 7.5 GY 5/6; 7.5 GY 6/6).

VIII. Pseudobracts:

A. *General.*—Paired, usually variegated, bract-like leaves, with reduced chartaceous blades and normally short petioles. They develop as opposite to subopposite pairs on a leafy stem and usually subtend a developing branch and/or cyathial branch.

B. *Shape.*—1. General: Variable from broadly ovate to reniform with orbicular tendencies. 2. Bract apices: Cuspidate to mucronate with occasional retuse mucronate and obcordate tendencies. 3. Bract bases: Usually cordate. 4. Bract margins: Entire with occasional revolute tendencies.

C. *Arrangement.*—Opposite to subopposite.

D. *Venation.*—Pinnately netted with a prominent midrib, the adaxial side having a tendency to be smooth and the abaxial side having a tendency to be ridged.

E. *Texture.*—Glabrous.

F. *Size.*—Usually 5–9 mm in diameter.

G. *Color.*—1. General: Commonly variegated with a basic generally reddish field that in color is usually dominated by a red, purplish red and/or purplish pink hue, the basic field having streaks and blotches which in color are usually dominated by a yellow green hue but nevertheless vary in pattern and size within any one pseudobract and from one to the next, the colors being somewhat obscured at the abaxial side of the blade by the translucent and glaucous nature of the lower epidermis. 2. Basic field: Commonly vivid red [11] (2.4 R 5.3/15.8; 3.5 R 4.9/16.6), deep purplish pink [248] (7.3 RP 6.0/14.3) and/or vivid purplish red [254] (0.3 R 4.8/16.1; 0.8 R 5.6/15.3; 8.8 RP 5.4/16.2; 9.9 RP 5.1/16.2). 3. Midvein and surrounding area: Commonly vivid yellow green [115] (5.4 GY 6.9/12.6; 5.4 GY 6.0/11.0) and/or strong yellow green [117] (3.3 GY 5.0/8.8; 3.7 GY 6.0/10.7; 5.3 GY 5.2/9.7; 5.4 GY 6.0/11.0). 4. Streaks and blotches: Commonly vivid yellow green [115] (2.6 GY 8.7/11.1; 3.9 GY 8.4/12.0; 5.4 GY 6.0/11.0; 5.4 GY 6.9/12.6), brilliant yellow green [116] (2.9 GY 8.8/9.8; 4.1 GY 8.6/10.3) and/or strong yellow green [117] (3.3 GY 5.0/8.8; 3.3 GY 6.0/10.7; 5.3 GY 5.2/9.7) and occasionally light yellow green [119] (2.9 GY 9.0/4.9) and pale yellow green [121] (3.7 GY 9.1/2.2; 4.9 GY 9.1/2.3).

IX. Inflorescences:

A. *General.*—Axillary and subtended by a normal leaf or pseudobract, the peduncle being commonly bifurcated and with each branch subtended by a membranous scale-like bract and bearing a terminal cyathium composed of two spreading colored bracts, several male flowers and usually a single central female flower although occasionally having a compound inflorescence created by development of the bract buds into a pair of pedunculate cyathia, thus forming a two tiered and occasionally a three tiered infloresence.

B. *Peduncle.*—1. General: Usually ascending from an axillary bud, being rigid and succulent, and usually bifurcated and bearing two cyathia. 2. Texture: Smooth and glabrous. 3. Shape: Terete with tendencies toward a slight increase in diameter distally for both the primary peduncle and the branches. 4. Size: (a) Length. [1] Primary axis: Usually 22–40 mm. [2] Branches: Usually 5–20 mm. (b) Diameter. [1] Primary axis: Usually 0.8–1.8 mm intermediate insertion and branches, and 1.2–1.8 mm across dichotomizing node. [2] Branches: Usually 0.4–0.8 mm just distally of furcation and expanding to 0.7–1.2 mm at the base of the cup formed by the cyathial bracts. [3] Exbracteate peduncle branches: Usually 7–15 mm just above the scale bract. 5. Color: Commonly vivid pink [1] (9.1 RP 6.9/11.1), deep pink [3] (0.8 R 6.2/13.3), and/or moderate red [15] (2.5 R 4/8; 2.5 R 4/10; 2.5 R 5/8).

C. *Pedicels.*—Long and slender for the male flower and strongly reduced and contiguous with the ovary of the female flower.

D. *Bracts of the Cyathium.*—1. General: Paired, valvate at the base of the infundibulum, and separating above with the enlargement of the involucre, each bract then becoming abruptly reflexed and expanded into half of a bilaterally symmetric disk of two. more or less reniform petaloid bracts. 2. Bract shape: (a) General. Reflexed and reniform with broadly ovate to cordate tendencies. (b) Blade apices. Broadly rounded with an abruptly mucronate to cuspidate tip that is penetrated by the midrib. (c) Blade bases. Broadly cordate and symmetric. (d) Blade margins. Entire. 3. Attachment: Opposite. 4. Venation: (a) General. Pinnately netted with inconspicuous lateral veins and prominent midrib. (b) Shape and arrangement. [1] Midrib: Tapering distally and being canaliculate at the adaxial side and prominently keeled at the abaxial side in the reflexed blade area. [2] Lateral Veins: Usually 7–9 secondary veins on each side of the midrib having an evidently smooth appearance but being rugose under magnification (10×) with the veins being raised on both the adaxial and abaxial sides at spaced intervals of 0.2–0.5 mm. [3] Midrib and vein colors: [a] General. Usually concolorous or nearly concolorous with the blade colors on the adaxial and abaxial sides. [b] Adaxial side. Commonly vivid purplish red [254] (0.03 R 4.8/16.9; 6.3 RP 4.7/18.0; 7.8 RP 4.4/17.0). [c] Abaxial side. Commonly strong purplish pink [247] (5.5 RP 7.1/10.0), light purplish pink [249] (5.4 RP 8.0/5.8) and/or pale purplish pink [252] (4.1 RP 8.7/2.9). 5. Petioles: (a) General. Chartaceous with each forming half of the cyathial infundibulum and merging into the expanded reflexed blade. (b) Shape. Plane and approximately trapezoidal when flattened and usually about 1.8–2.2 times broader than the width. (c) Texture. Glabrous and smooth on both adaxial and abaxial surfaces. (d) Size. [1] Width: Usually 3.8–4.5 mm at the base of the blade when flattened. [2] Length: Usually 1.8–3.5 mm (e) Color. [1] General: Usually much paler than either the peduncle or the bract blade. [2] Adaxial side: Commonly pale greenish yellow [104] (1.5 GY 9.1/4.0; 7.8 Y 9.0/4.0), pale yellow green [121] (2.1 GY 9.1/2.0; 2.5 GY 9/2; 10 Y 9/2). [3] Abaxial side: Commonly pale greenish yellow [104] (1.5 GY 9.1/4.0; 7.8 Y 9.0/4.0), pale yellow green [121] (2.1 GY 9.1/2.0; 2.5 GY 8.5/2; 10 Y 8.5/2; 10 Y 9.1/2.0). 6. Blades. (a) Sizes: [1] Length. Usually 3.5–6.5 mm. [2] Width (maximum). Usually 5–8 mm. (b) Color: Color dominated by a red and/or purplish red hue when blades are mature and fully expanded. Commonly vivid red [11] (1.6 R 4.4/16.1; 2.4 R 5.3/15.8) and/or vivid purplish red [254] (0.3 R 4.8/16.9; 0.8 R 5.6/15.3; 8.8 RP 5.4/16.2; 9.9 RP 5.1/16.2) when mature and fully expanded, and usually deep pink [3] (0.8 R 6.2/13.3; 9.4 RP 6.2/13.5) during immaturity.

E. *Involucre.*—1. General: Campanulate, chartaceous, and ten-lobed distally, each lobe having a single midian main vein and alternate lobes being glandular and separated by fimbriate, befid lobes. 2. Involucral Cup: (a) General. Campanulate with ten marginal appendages. (b) Texture. Glabrous and chartaceous. (c) Size. [1] Diameter (across open end): Usually 2.8–3.2 mm. [2] Height (bract bud to distal sinus): Usually 2.5–3.1 mm. [3] Color: Commonly light greenish yellow [101] (0.6 GY 9.0/7.8; 7.5 Y 8.8/7.2), pale greenish yellow [104] (1.5 GY 9.1/4.0; 7.8 Y 9.0/4.0) light yellow green [119] (2.9 GY 9.0/4.9) and/or pale yellow green [121] (2.1 GY 9.1/2.0; 3.7 GY 9.1/2.2) with the colors tending to be more intense distally. 3. Glands: (a) General. Reniform on a broad short stipe extending upwardly from the margin of the involucral cup, the secretory surface of the gland being in the shallow distal groove. (b) Size: [1] Width (tangential). Usually about 0.8–1.2 mm. [2] Height. Usually about 0.6–1.0 mm. [3] Thickness (radial). Usually 0.25–0.4 mm. (c) Color: [1] Stipe. Usually more intensely pigmented than the upper part of the involucral cup and commonly brilliant yellow green [116] (4.2 GY 8.7/9.4; 6/4 GY 8.6/8.2; 6.5 GY 8.5/9.5). [2] Glands. Commonly vivid yellow [82] (2.9 Y 8.2/12.2: 3.7 Y 7.9/15.1; 6.6 Y 8.6/11.4: and/or brilliant yellow [83] (3.2 Y 8.4/9.8 when active during the pollen reception stage and vivid red [11] (1.6 R 4.4/16.1; 3.6 R 4.0/15.7; 4.4 R 3.7; 15.0), vivid purplish blue [194] (7.8 RP 4.4/17.0), vivid violet [205] (9.7 RP 4.0/16.0) and/or vivid purplish red [254] (9.7 RP 4.0/16.0) during the pollen presentation stage. 4. Fimbriate lobes. (a) General: Alternate to glandular lobes and involute with respect to the involucral cup margin. (b) Shape: Broadly obcordate distally of a wide stipe, and each of the two distal lobes being fimbriate and having 7–10 segments. (c) Size: [1] Width. Usually 1.0–1.3 mm. [2] Height. Usually 1.0–1.3 mm. (d) Color: [1] Distal lobes. Commonly vivid red [11] (2.4 R 5.3/15.8; 4.3 R 5.5/15.6; 5.6 R 5.2/16.4). [2] Stipe. Commonly light greenish yellow [101] (0.6 GY 9.0/7.8) and/or pale greenish yellow [104] (1.5 GY 9.1/4.0; 7.8 Y 9.0/4.0).

F. *Flowers.*—1. General. Monoecious with each cyathium bearing a single central female flower which matures prior to the male flowers and is surrounded by numerous single stamen male flowers that are each subtended by hairlike bracteoles and mature only after the stigmas are no longer receptive. 2. Female flowers. (a) General: Consists of a single gynoecium borne on a short pedicel. (b) Gynoecium: [1] General. Compound, the ovary usually composed of three glabrous fused carpels and with separate styles and stigmas. [2] Stigma. [a] General: Bifid with wide spreading segments. [b] Size: About 0.1 mm long. [c] Color: Commonly vivid red [11] 5.5 R 2.9/11.6), deep red [13] (near 4.0 R 2.3/8.5) and dark red [16] (near 4.0 R 2.3/8.5; 5.5 R 2.4 R 2.4/8.5). [3] Style. [a] General: One per carpel, curved and wide spreading when pollen receptive and later becoming straight, almost erect from the ovary and with slight spreading separating the stigmas. [b] Size: Each about 1.8–2.2 mm long. [c] Color: Commonly pale pink [7] (9.3 RP 8.6/2.9), light purplish pink [249] (7.5 RP 8.0/5.6) and/or pale purplish pink [252] (7.5 RP 8.6/3.0). [4] Ovary. [a] General: Globose with longitudinal grooves where the three carpels are fused and with each carpel producing a single seed upon maturity. [b] Size: Usually 1.0–1.3 mm high and 0.8–1.2 mm in diameter. [c] Color: Commonly brilliant yellow green [116] (2.9 GY 8.8/9.8; 4.1 GY 8.6/10.3; 4.2 GY 8.79/9.4). [5] Pedicel: [a] General. Short cylindric and grabrous. [b] Size. Usually 0.4–0.6 mm long and 0.2–0.4 mm in diameter. [c] Color. Usually concolorous with ovary and commonly brilliant yellow green [116] (2.9 GY 8.8/9.8; 4.1 GY 8.6/10.3; 4.2 GY 8.7/9.4). 3. Male Flowers: (a) General. Consists of a single stamen borne on a stalk-like pedicel which extends above the ovary and is subtended by hairlike bracteoles, only one to three male flowers usually releasing pollen at any one time in a cyathium. (b) Stamens. [1] General: Anther sacs are at angles to the filament, forming a "T" or "Y". [2] Filaments: [a] General. Erect, glabrous and terete. [b] Size. Usually 0.8–1.6 mm long and about 0.1 mm or less in diameter. [c] Color. Translucent and commonly yellowish white [92] (10 Y 9/1) and/or pale yellow green [121] (2.1 GY 9.1/2.0; 2.5 GY 9/2; 10 Y 9.1/1.9). [9] Anther: [a] General. Pollen sacs are separated by a connective set transverse to the filament and dehiscence occurs by rupture of the stomial groove on the distal face of the pollen sac. [b] Shape and Texture. Glabrous and usually pyriform to obovoid from the site of insertion at the top of the filament. [c] Size. Usually 0.8–1.2 mm across the widest part of the anther and with the pollen sacs being about 0.4–0.7 mm long. [d] Color. (1) Connective: Commonly yellowish white [92] (10 Y 9/1). (2) Pollen sacs (before pollen release): Commonly vivid red [11] (1.6 R 4.4/16.1; 3.6 R 4.0/15.7) and/or vivid purplish red [254] (0.3 R 4.8/16.9; 7.8 RP 4.4/17.0; 9.7 RP 4.0/16.0). (3) Pollen: Commonly light greenish yellow [101] (10 Y 9/6) and/or pale greenish yellow [104] (10 Y 9/4). (c) Pedicel. [1] General: Elongate, terete and glabrous. [2] Size: Usually 2.5–3.5 mm long and about 0.1 mm in diameter. [3] Pollen: Commonly pale yellow [89] (near 7.5 Y 9/2), yellowish white [92] (near 7.5 Y 9/2; 10 Y 9/1) and/or pale yellowish green [121] (2.5 GY 9/2).

X. Growth habit: Among others evident from the foregoing, a very compact growth habit with short internodes and frequent branching of clavate branches and from a single propagated cutting being productive of a specimen with a compact dome shaped vegetative crown without the need for pruning, the specimens having paseudobracts which are commonly variegated and carry buds that are able to develop into spiny branches or cyathial branches.

PROPAGATION AND GROWING PROCEDURE

The soil preparation used for the propagation of the new variety specimens from which the description was taken comprised a 40–60% (by volume) admixture of perlie and Canadian Peat. Propagation was originally accomplished during the middle of April by planting 7–10 cm stem cuttings about 5 cm deep in three inch growing pots containing the soil preparation. Until transplanted, the cuttings were daily subjected to 5 seconds of a water mist every 5 minutes from 8:00 A.M. to 5:00 P.M.

The rooted cuttings were transplanted to six inch growing pots during the first week of August following propagation and were again transplanted to eight inch growing pots during the last week of October and wherein they were retained until observed.

The soil preparation used in the transplantings was the same as that used for propagation except it also contained a slow release 14–14–14 ($N$–$P_2O_5$–$K_2O$) fertilizer in amounts equivalent to 9 pounds of fertilizer per cubic yard of soil preparation and a trace element additive in amounts equivalent to 1 pound of additive per cubic yard of soil preparation. The "trace element additive" referred to had a reported elemental analysis of: S (12%), B (0.1%), Cu (0.5%), Fe (12.0%), Mn (2.5%), Mo (0.05%) and Zn (1.0%) and wherein the elements are derived from sodium borate, copper sulfate, ferrous sulfate, manganese sulfate, sodium molybdate and zinc sulfate.

Throughout the growing period, the plants were watered daily and fertilized every six weeks with a small amount of a dry granular 16–3–3 ($N$–$P_2O_5$–$K_2O$) fertilizer. Propagation and growth was carried out in full sunlight (unshaded) nursery conditions in the Hollywood, Fla. area and wherein temperatures during the growing period ranged from 39°–97° F.

DESCRIPTION OF A SPECIMEN

The following is a general description of a specimen of the new plant variety which was grown in a nursery at Hollywood, Fla. from a propagated stem cutting and wherein the description was taken in the month of June.

I. General:

A. *Age of specimen.*—6 months from initial propagation.

B. *Height of specimen (leafy crown).*—150 mm.

C. *Diameter of specimen (leafy crown).*—170 mm.

D. *Number of primary branches.*—16.

E. *Total number of branches with mature leaves.*—67.

F. *Number of mature cyathial inflorescences.*—98.

II. Stems and branches:

A. *Main axis.*—1. Height (above soil line). 150 mm. 2. Diameter (1–3 cm above soil line). 11 mm. 3. Color. (a) Basal area: Yellowish gray [93] (5 Y 7/1). (b) Apical area: Light olive [106] (10 Y 6/4), dark greenish yellow [103] (10 Y 6/6) and moderate greenish yellow [102] (10 Y 7/6).

B. *Primary branches.*—1. Length. Varies from 55–130 mm. 2. Diameter. Varies from 4–6 mm near insertions to 8–10 mm near distal end. 3. Color. (a) Basal areas: Yellowish gray [93] (near 2.5 Y 7/2; 5 Y 7/1), grayish yellow [90] (near 2.5 Y 7/2). (b) Apical areas: Light olive [106] (10 Y 6/4; 7.5 Y 5/4), dark greenish yellow [103] (10 Y 6/6), moderate greenish yellow [102] (10 Y 7/6) and moderate yellow green [120] (2.5 GY 7/6).

C. *Secondary branches.*—1. Length. Varies from 40–90 mm. 2. Diameter. Varies from 2–4.0 mm.

III. Mature leaves:

A. *Petioles.*—1. Diameter. Varies from 1.0–1.5 mm. 2. Length (proximal to extension of decurrent blade base). Varies from 0.5–1.5 mm. 3. Color. (a) Adaxial sides: Light yellow green [119] (5 GY 9/4) and brilliant yellow green [116] (5 GY 8/8; 5 GY 8/10). (b) Abaxial sides: Deep greenish yellow [100] (near 10 Y 6/8), dark greenish yellow [103] (near 10 Y 6/8), light yellow green [119] (2.5 GY 8/6) and moderate yellow green [120] (2.5 GY 6/6; 2.5 GY 6/7).

B. *Midribs.*—1. Color. (a) Adaxial sides: Deep yellow green [118] (6.5 GY 3.8/7.1), moderate olive green [125] (6.1 GY 3.2/5.8), and dark yellowish green [137] (8.2 GY 3.2/6.1; 9.3 GY 3.0/6.8). (b) Abaxial sides: Strong yellow green [117] (near 5.0 GY 4.5/8.2), deep yellow green [118] (near 5.0 GY 4.5/8.2), deep yellow green [118] (6.5 GY 3.8/7.1) and moderate olive green [125] (4.5 GY 3.9/6.9; 6.1 GY 3.2/5.8).

C. *Blades.*—1. Lengths. Vary 25–43 mm. 2. Widths. Vary 13–18 mm. 3. Color. (a) Adaxial sides: Deep yellow green [118] (6.5 GY 3.8/7.1) and moderate olive green [125] (4.5 GY 3.9/6.9; 6.1 GY 3.2/5.8). (b) Abaxial sides: Strong yellow green [117] (2.5 GY 4.6/7.7; 3.3 GY 5.0/8.8; 5.3 GY 5.2/9.7) and moderate yellow green [120] (5 GY 6/6; 7.5 GY 5/6).

IV. Pseudobracts:

A. *Sizes.*—Vary 5–8 mm in diameter.

B. *Colors.*—1. Basic fields. Vivid red [11] (2.4 R 5.3/15.8; 3.5 R 4.9/16.6), deep purplish pink [248] (7.3 RP 6.0/14.3) and vivid purplish red [254] (0.3 R 4.8/16.1; 0.8 R 5.6/15.3; 8.8 RP 5.4/16.2; 9.9 RP 5.1/16.2). 2. Midvein areas. Vivid yellow green [115] (5.4 GY 6.9/12.6; 5.4 GY 6.0/11.0) and strong yellow green [117] (3.3 GY 5.0/8.8; 3.7 GY 6.0/10.7; 5.3 GY 5.2/9.7; 5.4 GY 6.0/11.0). 3. Streaks and blotches. Vivid yellow green [115] (2.6 GY 8.7/11.1; 3.9 GY 8.4/12.0; 5.4 GY 6.0/11.0; 5.4 GY 6.9/12.6), brilliant yellow green [116] (2.9 GY 8.8/9.8; 4.1 GY 8.6/10.3) and strong yellow green [117] (3.3 GY 5.0/8.8; 3.3 GY 6.0/10.7; 5.3 GY 5.2/9.6).

V. Inflorescences:

A. *Peduncles.*—1. Sizes. (a) Lengths: [1] Primary axes. Vary 22–35 mm. [2] Branches. Vary 7–18 mm. (b) Diameters: [1] Primary axes (intermediate insertion and branches). Vary 1–1.8 mm. [2] Branches (just distally of furcation). Vary 0.5–0.8 mm. 2. Colors. Moderate red [15] (2.5 R 4/8; 2.5 R 4/10).

B. *Bracts of the cyathium.*—1. Petioles (mature blades, e.g. fully expanded). (a) Sizes: [1] Widths (at base of blade when flattened). Vary 3.9–4.5 mm. [2] Lengths. Vary 2.0–3.5 mm. (b) Colors. Pale greenish yellow [104] (1.5 GY 9.1/4.0; 7.8 Y 9.0/4.0) and pale yellow green [121] (2.1 GY 9.1/2.0; 10 Y 9.1/1.9). 2. Blades (mature blades, e.g. fully expanded). (a) Sizes: [1] Widths (maximums). Vary 6–8 mm. [2] Lengths. Vary 4–6 mm. (b) Colors. Vivid red [11] (2.4 R 5.3/15.8) and vivid purplish red [254] (0.3 R 4.8/16.9; 0.8 R 5.6/15.3; 8.8 RP 5.4/16.2; 9.9 RP 5.1/16.2).

C. *Involucre.*—1. Involucral cups. (a) Sizes: [1] Diameters (across open end): Most about 3.0 mm. [2] Heights (bract bud to distal sinus): Most about 3.0 mm. (b) Colors. Light yellow green [119] (2.9 GY 9.0/4.9) and pale yellow green [121] (2.1 GY 9.1/2.0; 3.7 GY 9.1/2.2). 2. Glands. (a) Sizes: [1] Heights. Most about 0.8 mm. [2] Widths (tangential). Most about 1 mm. [3] Thicknesses (radial). Most about 0.3 mm. (b) Colors: Varies with pollen reception or presentation. Vivid yellow [82] (3.7 Y 7.9/15.1; 2.9 Y 8.2/12.2), brilliant yellow [83] (3.2 Y 8.4/9.8), vivid red [11] (3.6 R 4.0/15.7; 4.4 R 3.7/15.7) and vivid purplish red [254] (9.7 RP 4.0/16.0). 3. Fimbriate lobes. (a) Sizes: [1] Widths. Most about 1.1 mm. [2] Heights. Most about 1 mm. (b) Color of lobes: Deep purplish pink [242] (7.3 RP 6.0/14.3), strong purplish pink [247] (5.9 RP 6.7/12.2; 8.0 RP 6.8/11.4) and vivid purplish red [254] (8.8 RP 5.4/16.2).

D. *Flowers.*—1. Female flowers. (a) Size: [1] Height (pedicel and pistil). Most about 4 mm. [2] Ovary diameters: Most about 1.0 mm before pollination. (b) Colors. [1] Stigmas: Vivid red [11] (5.5 R 2.9/11.6). deep red [13] (near 4.0 R 2.3/8.5) and dark red [16] (near 4.0 R 2.3/8.5; 5.5 R 2.4/8.5). [2] Styles: Pale pink [7] (9.3 RP 8.6/2.9), light purplish pink [249] (7.5 RP 8.0/5.6) and pale purplish pink [252] (7.5 RP 8.6/3.0). [3] Ovary: Brilliant yellow green [116] (4.1 GY 8.6/10.3; 4.2 GY 8.7/9.4). 2. Male flowers: (a) Sizes: [1] Heights (including pedicel, filament and anther): Vary 4–5 mm. [2] Pedicel diameters: most about 0.1 mm. [3] Filament diameters: Most about 0.1 mm. [4] Anther widths (maximums): Vary 0.8–1.0 mm. [5] Pollen sac lengths: Most about 0.5 mm. (b) Colors. [1] Filaments and Pedicels: Yellowish white [92] (10 Y 9/1) and pale yellowish green [121] 92.5 GY 9/2). [2] Anthers: Vivid red [11] (1.6 R 4.4/16.1; 3.6 R 4.0/15.7) and vivid purplish red [254] (9.7 RP 4.0/16.0) prior to pollen release. [3] Pollen: Light greenish yellow [101] (10 Y 9/6) and pale greenish yellow [104] (10 Y 9/4).

I claim:

1. The new and distinct variety of Euphorbia plant substantially as herein shown and described and which is principally distinguishable by a growth habit that combines the following characteristics:

(a) compactness with short internodes and very frequent branching;

(b) branches which are clavate and at the nodes bear persistent long acicular stipular spines that are usually 8–12 mm in length;

(c) leaves which in shape generally range from oblanceolate to obovate, and have relatively short petioles and blades that in length are usually 25–45 mm and in maximum width are usually 12–18 mm;

(d) pseudobracts which usually develop as opposite to subopposite pairs on a leafy stem or branch, subtend a developing leafy branch and/or cyathial branch, and have blades that are usually variegated and provided with a basic field which in color is dominated by a red, purplish red and/or purplish pink hue and has streaks and/or blotches that vary in pattern and size within a pseudobract and/or from one pseudobract to the next and in color is usually dominated by a yellow green hue;

(e) an inflorescence which rarely has more than three tiers of cyathia and wherein the blades of the cyathial bracts are in color dominated by a red and/or purplish red hue when mature and fully expanded; and (f) specimens which when derived by the propagation of a single stem cutting have a dense interlocked network of branches that provide a compact domed vegetative crown without the need for pruning.

* * * * *

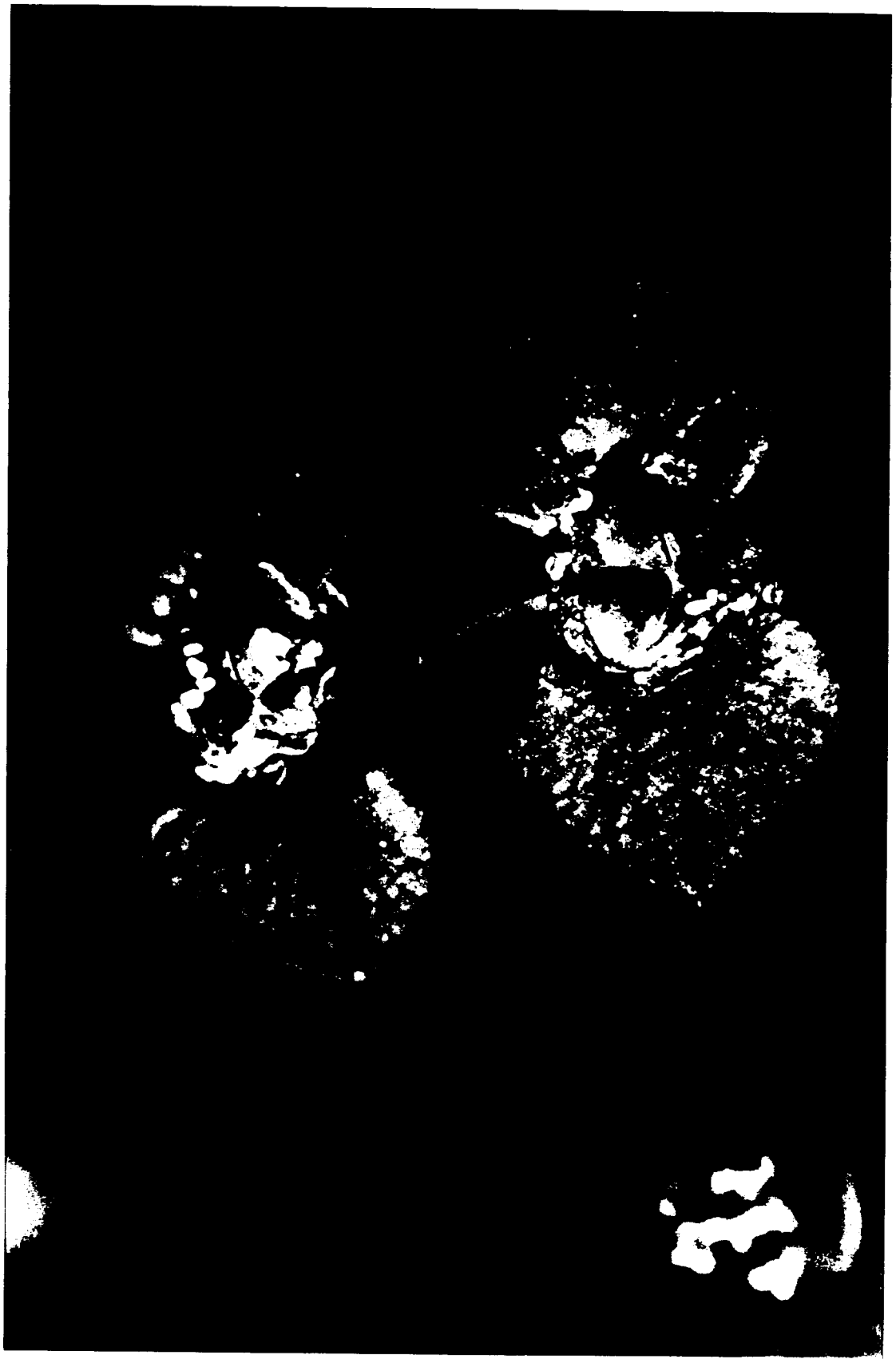

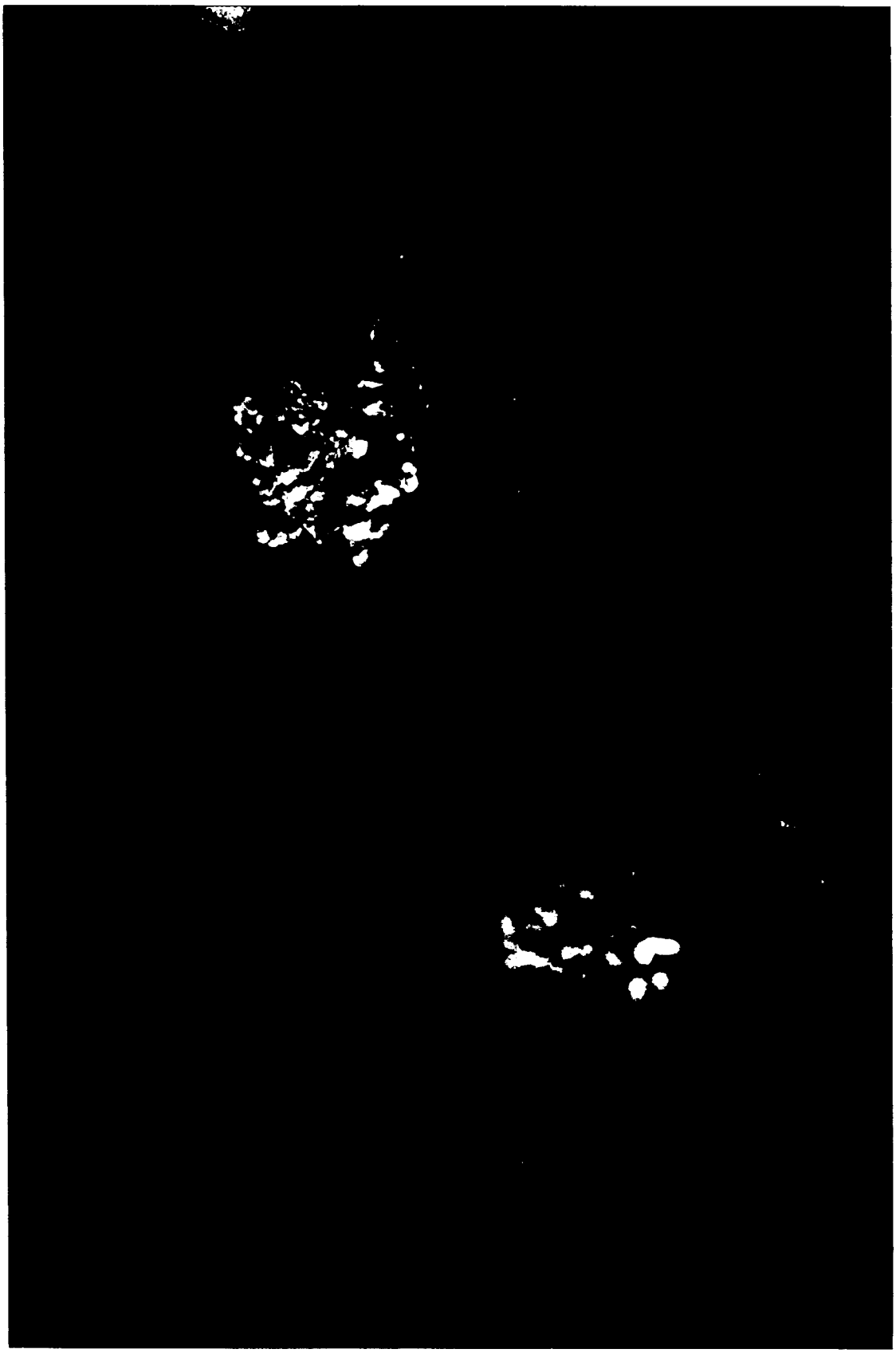

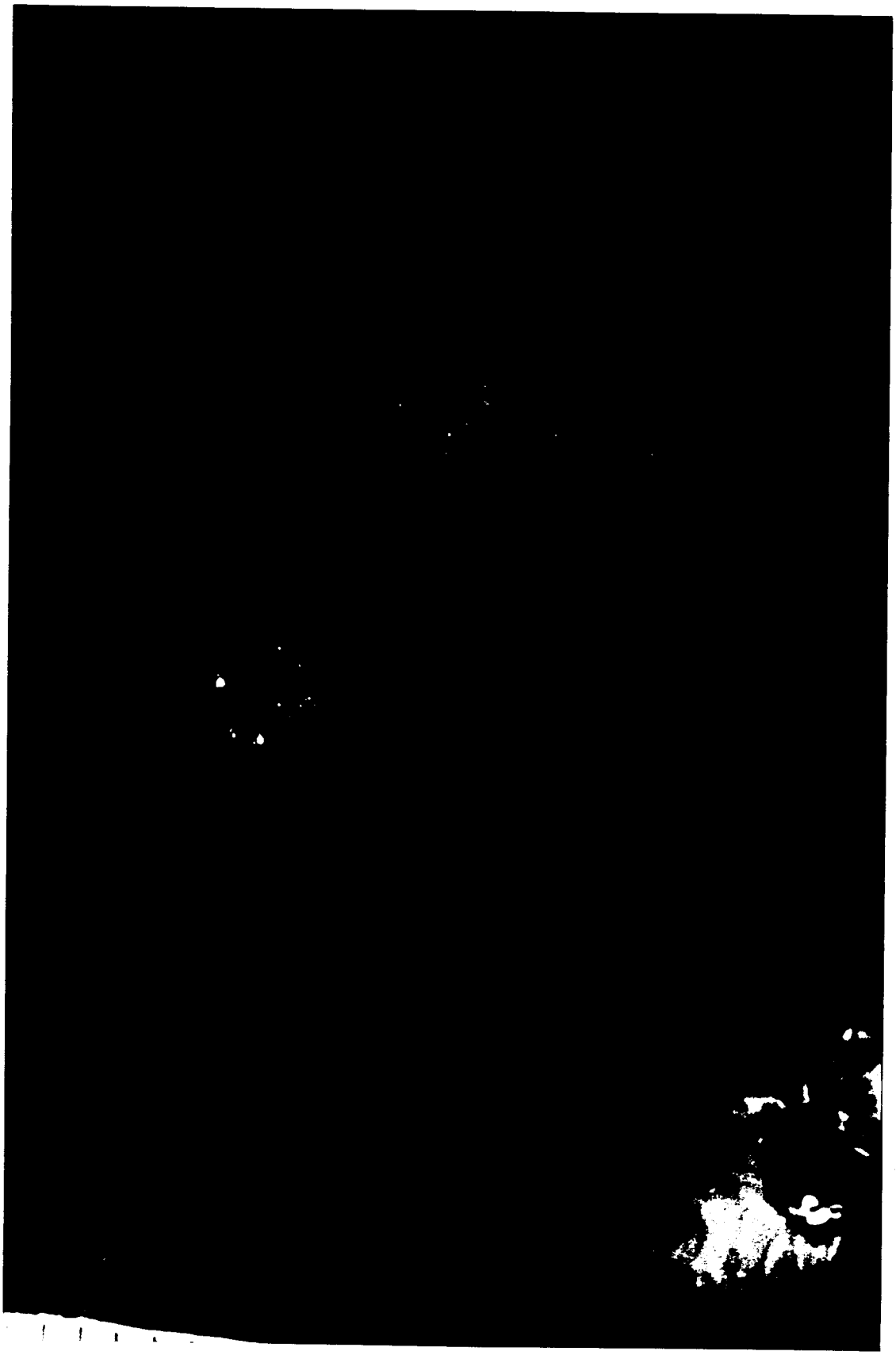

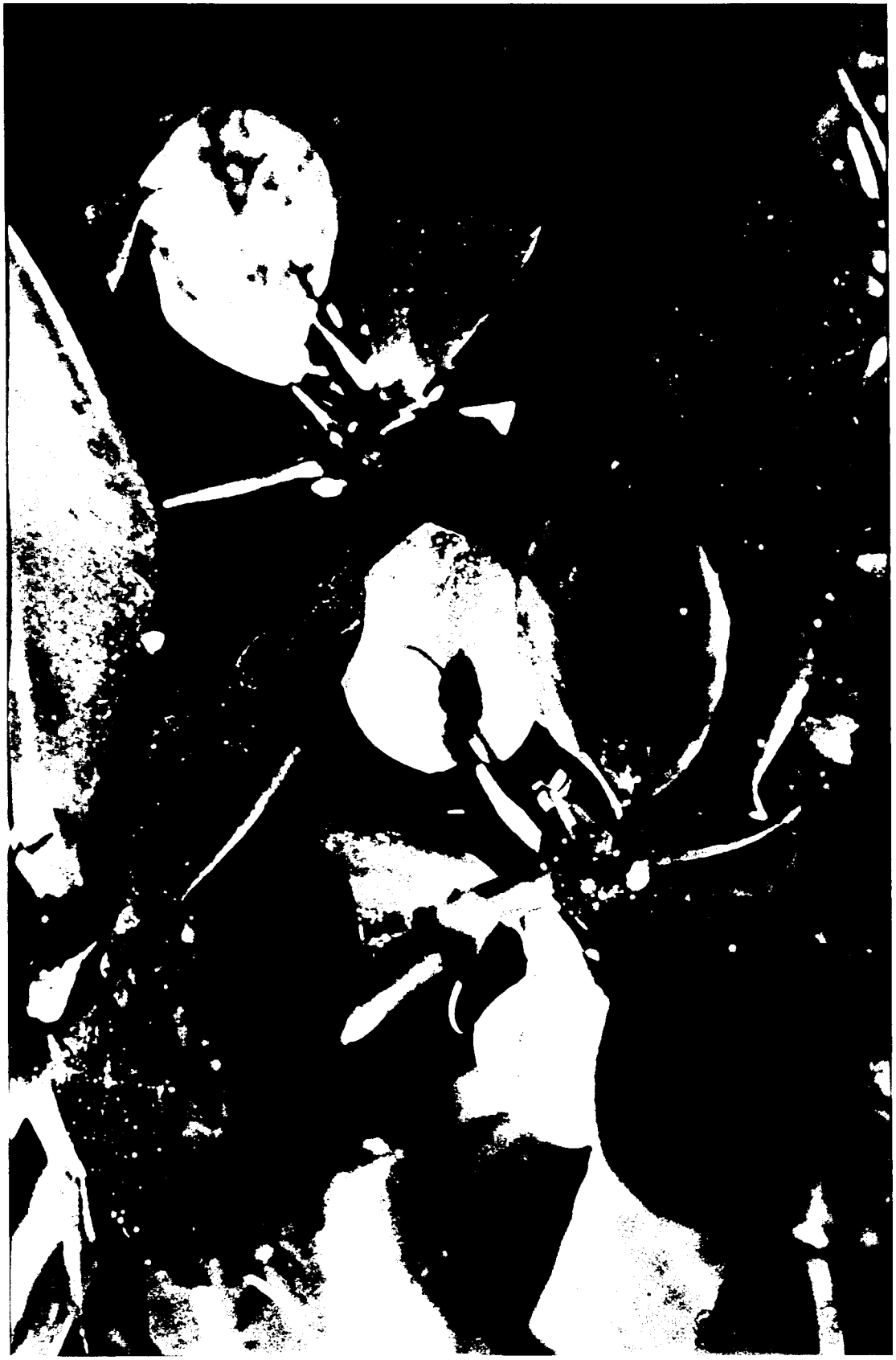

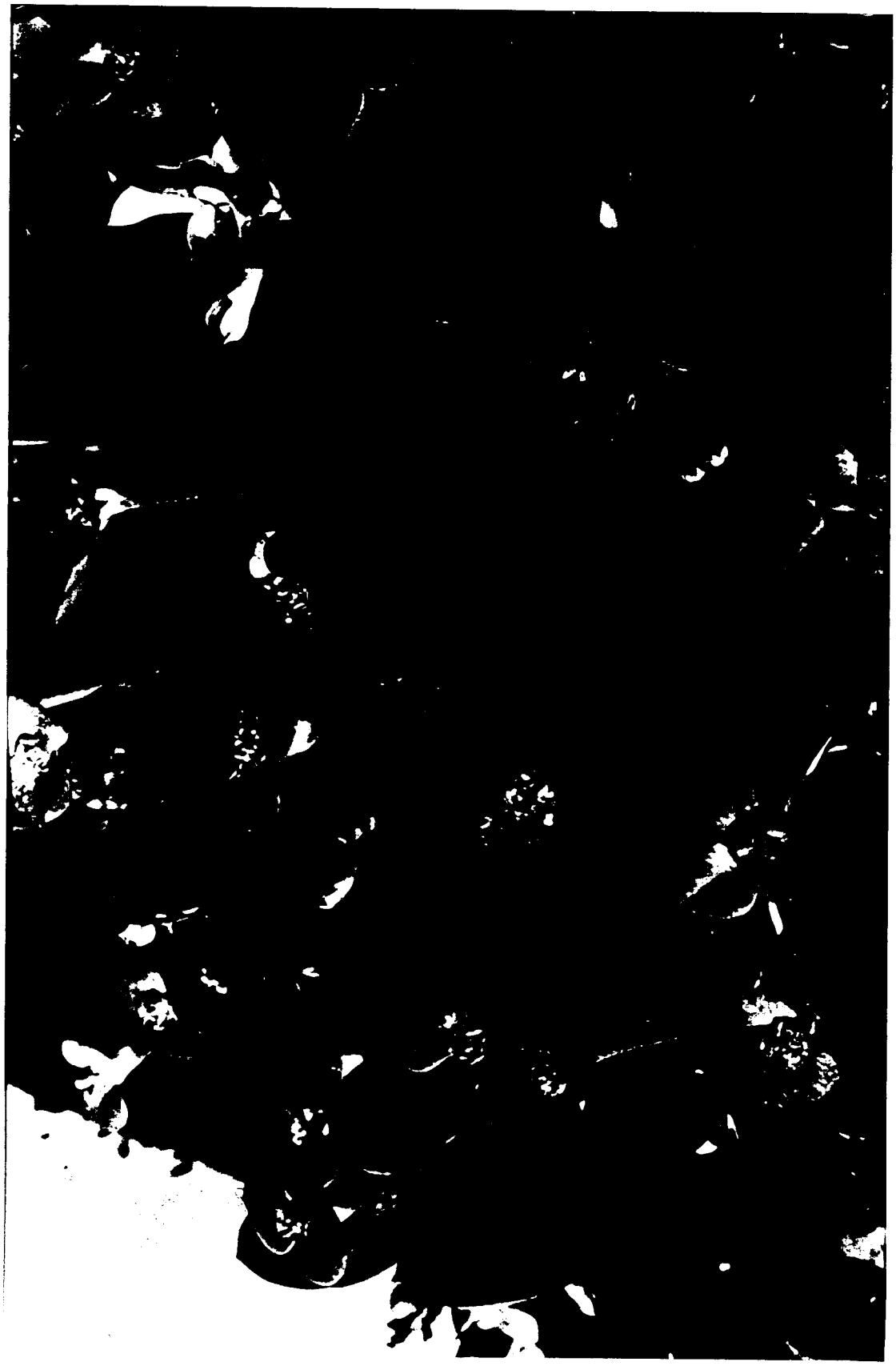

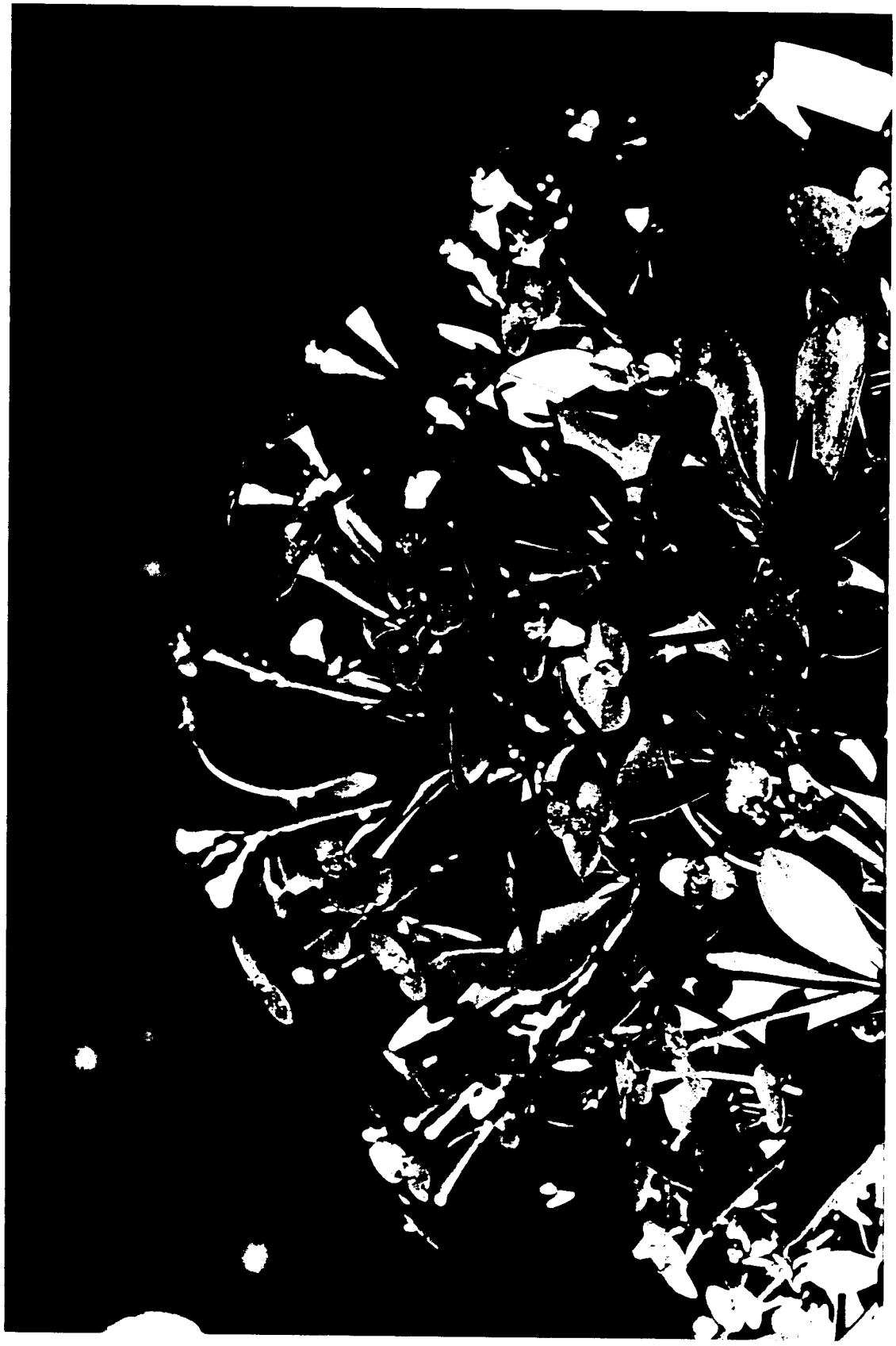

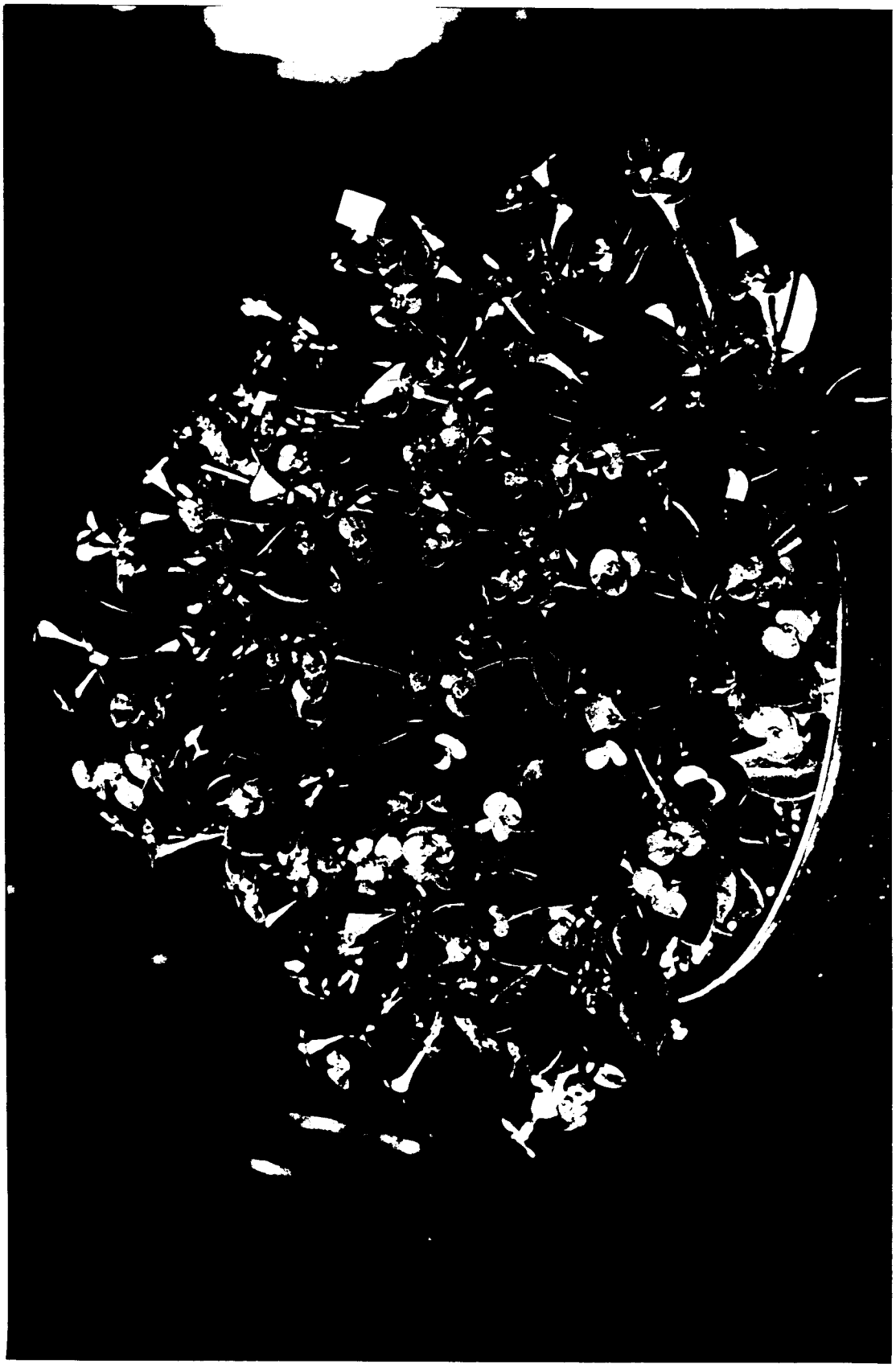

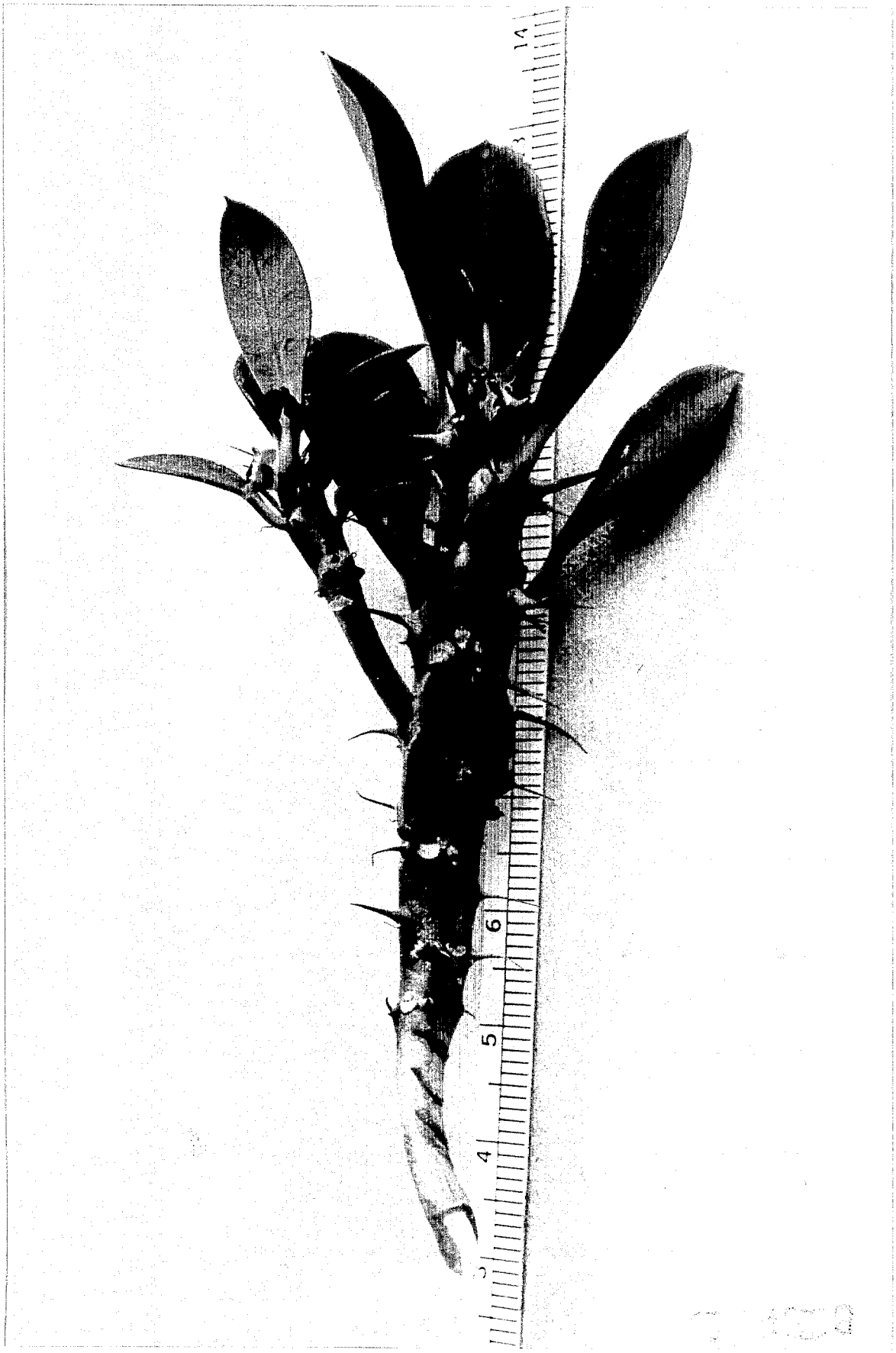
14
13
6
5
4
3